United States Patent [19]
Nakamura et al.

[11] Patent Number: 5,644,393
[45] Date of Patent: Jul. 1, 1997

[54] EXTRANEOUS SUBSTANCE INSPECTION METHOD AND APPARATUS

[75] Inventors: Hisato Nakamura, Saitama-ken; Tetsuya Watanabe; Yoshio Morishige, both of Honjo, all of Japan

[73] Assignee: Hitachi Electronics Engineering Co., Ltd., Tokyo, Japan

[21] Appl. No.: 678,069

[22] Filed: Jul. 10, 1996

[30] Foreign Application Priority Data

Oct. 19, 1995 [JP] Japan ................. 7-296065

[51] Int. Cl.[6] .................................. G01N 21/89
[52] U.S. Cl. ........................ 356/237; 250/559.45
[58] Field of Search ..................... 356/237, 426, 356/338, 446; 250/559.45, 559.46, 559.47, 559.48, 559.49, 548

[56] References Cited

U.S. PATENT DOCUMENTS

| | | | |
|---|---|---|---|
| 4,659,172 | 4/1987 | Cavan | 350/3.83 |
| 4,794,264 | 12/1988 | Quackenbos et al. | 250/563 |
| 5,377,002 | 12/1994 | Malin et al. | 356/237 |
| 5,481,202 | 1/1996 | Frye, Jr. | 324/754 |

*Primary Examiner*—Frank Gonzalez
*Assistant Examiner*—Zandra V. Smith
*Attorney, Agent, or Firm*—Fay, Sharpe, Beall, Fagan, Minnich & McKee

[57] ABSTRACT

In the present invention, an extraneous substance inspection optical system having an extraneous inspection area of a predetermined scanning width in subscanning direction of a matter to be inspected is positioned in such a manner that the extraneous substance inspection area at a moment when the matter to be inspected is started to move in main scanning direction is arranged at a position in the main scanning direction corresponding to a head portion of the matter to be inspected; the matter to be inspected is moved in the main scanning direction to be subjected to a forward scanning for the matter to be inspected to thereby detect possible extraneous substances in the extraneous inspection area; and the matter to be inspected is rotated by 180° after completing the forward scanning, then the matter to be inspected is moved in the direction opposite to the forward scanning to be subjected to a backward scanning, to thereby detect possible extraneous substances in the extraneous substance inspection area.

10 Claims, 5 Drawing Sheets

EXTRANEOUS SUBSTANCE INSPECTION METHOD AND APPARATUS

BACKGROUND OF THE INVENTION

1. Field of the Invention

The present invention relates to an extraneous substance inspection method and apparatus and, more specifically, relates to an extraneous substance inspection method and apparatus for semiconductor wafers in which a moving range of an inspection table is reduced to thereby limit the size of the inspection table and to improve the inspection efficiency.

2. Background Art

There are two types of extraneous substance inspection apparatus for semiconductor wafers (hereinafter simply called as wafer or wafers), one is that which employs an XY scanning method in which laser beam is irradiated over the surface of a wafer so as to scan the same in X and Y directions, and the other is that which employs a rotating scanning method in which laser beam is irradiated over the surface of a wafer while rotating the same so as to scan the same in a manner of a spiral shape or a concentric circular shape.

In the former XY scanning, for example, an inspection table is moved in X direction for performing a main scanning, and laser beam or further the inspection table is moved in Y direction for performing a subscanning. The main scanning in X direction is normally a reciprocating scanning in order to enhance the scanning speed. Although the XY scanning method poses a problem of requiring a long time for scanning over the entire surface of a wafer, however, has advantages that the detection accuracy at individual detection areas is invariable and comparatively small extraneous substances can be detected with accurate locations thereof. On the other hand, in the latter scanning method since the circumferential velocities at the outer circumference on a wafer and at the center portion thereon are different, the latter poses a problem with regard to non-uniform detection at the individual detection areas that the scanning density at the outer circumferences is rough, and the scanning density at the center portion thereof is dense and further the detection areas therearound overlap each other, however the latter has an advantage that the time required for the scanning over entire surface of the wafer is shortened.

In these days, in association with the improvement in integration degree of ICs an improvement in inspection accuracy of a wafer is demanded. In connection thereto, the XY scanning method tends to be used for performing the extraneous substance inspection for wafers. However, when an extraneous substance inspection is performed in a semiconductor manufacturing process line by incorporating therein an extraneous substance inspection apparatus employing an XY scanning method, the through-put due to the inspection reduces and, in addition, a drawback of increasing the size of the apparatus is caused which will be explained below.

FIG. 5 is a view for explaining a moving range of an inspection table in a conventional extraneous substance inspection apparatus employing an XY scanning method. A wafer 1 is carried on the inspection table, however, in the drawing the moving range of the inspection table is explained by making use of the movement of the wafer 1.

When assuming that an extraneous substance inspection optical system 2 is set at the position as illustrated, in order to scan the entire surface of the wafer 1 it is necessary to move the wafer 1 with the inspection table in such a manner that the center 0 of the wafer 1 moves in X direction from axis X1 to X2. With regard to Y direction the wafer 1 has to be moved with the inspection table in such a manner that the center 0 of the wafer 1 moves a distance corresponding to that from axis Y1 to axis Y2.

Accordingly, when assuming that the diameter of the wafer 1 is D, if the inspection table carrying the wafer 1 does not cover at least a range 2D×2D, in that logitudinally 2D and laterally 2D, the entire surface scanning through the movement of the wafer can not be achieved. For this reason, it is necessary to enlarge the size of the movement mechanism for the extraneous substance inspection table at least more than the range of 2D×2D. Therefore, it was inavoidable to increase the size of the apparatus including the inspection table. In particular, there arises a problem that the size of the apparatus increases corresponding to the increase of the outer diameter of the wafer 1.

On the other hand, instead of moving the wafer 1 if the extraneous substance inspection optical system is moved to scan the wafer 1, the moving range of the scanning system decreases. However, because the extraneous substance inspection optical system includes a lot of lenses therein, a high speed movement of the extraneous substance inspection optical system itself likely causes such as a positional displacement and vibration of the optical system which disturbs an accurate extraneous substance detection. Further, in view of the size and weight of the optical system such high speed movement is not preferable.

Different from the above measure there is another method in which a wafer is scanned by swinging laser beam, however, such method increases the scale of the scanning optical system and the entire size of the apparatus inavoidable increases.

SUMMARY OF THE INVENTION

An object of the present invention is to provide an extraneous substance inspection method in which a moving range of an inspection table is halved to about two times of the diameter of a wafer to thereby reduce the size of the apparatus therefor as well as enhance the inspection efficiency thereof.

Another object of the present invention is to provide an extraneous substance inspection apparatus in which the size of an inspection table is limited to thereby reduce the size of the apparatus as well as enhance the inspection efficiency thereof.

An extraneous substance inspection method which achieves the above object is characterized, in that the method comprises the steps of: positioning an extraneous substance inspection optical system having an extraneous inspection area of a predetermined scanning width in sub-scanning direction of a matter to be inspected in such a manner that the extraneous substance inspection area at a moment when the matter to be inspected is started to move in main scanning direction is arranged at a position in the main scanning direction corresponding to a head portion of the matter to be inspected; moving the matter to be inspected in the main scanning direction to perform a forward scanning for the matter to be inspected; rotating the matter to be inspected by 180° after completing the forward scanning; then moving the matter to be inspected in the direction opposite to the forward scanning to perform a backward scanning, whereby possible extraneous substances in the respective extraneous substance inspection areas are detected.

Further, an extraneous substance inspection apparatus according to the present invention is characterized, in that the apparatus comprises: an extraneous substance inspection optical system having an extraneous inspection area of a predetermined scanning width in subscanning direction of a matter to be inspected and positioned in such a manner that the extraneous substance inspection area at a moment when the matter to be inspected is started to move in main scanning direction is arranged at a position in the main scanning direction corresponding to a head portion of the matter to be inspected; a moving and rotating mechanism which mounts the matter to be inspected thereon, moves reciprocatively the matter to be inspected in main scanning direction and rotates the matter to be inspected by substantially 180° around the substantial center thereof; and a control unit which controls the moving and rotating mechanism in such a manner that the matter to be inspected is performed a forward scanning in the main scanning direction, rotated by 180° after completing the forward scanning in the main scanning direction and further performed a backward scanning in the main scanning direction, whereby possible extraneous substances in the respective extraneous substance inspection areas are detected via the forward scanning and the backward scanning. The extraneous substances referred to above include flaws on the surface of the matter to be inspected.

Namely, the extraneous substance inspection optical system is disposed at a position in the main scanning direction corresponding to the head portion of the matter to be inspected at the moment when the matter to be inspected is started to move, the matter to be inspected is moved to be subjected to a main scanning in only one of X direction and Y direction and after completing a forward main scanning the matter to be inspected is rotated by 180° around the center thereof then a backward scanning for the matter to be inspected is initiated, for example, after rotating a wafer by 180° around the center thereof the backward scanning therefor is initiated. Thereby, the starting point of the backward scanning on the wafer corresponds to the point symmetric position of the position at which the forward main scanning has been completed and the backward scanning area is varied from the forward scanning area.

Since the wafer is configured substantially circular, no bulging-out or increase of the wafer covering area occurs in the subscanning direction perpendicular to the main scanning direction before and after the rotation of 180°.

Further, even if the matter to be inspected is a rectangular shape such as, for example, LCD substrate other than the circular wafer, no substantial increase of the covering area occurs in the subscanning direction before and after the rotation thereof around the center thereof and the covering area is likely limited to the length of the one side of the rectangular substrate in the subscanning direction. Accordingly, the scanning range in the subscanning direction is substantially halved in comparison with a case wherein the scanning is performed from one end of the one side to other end thereof. Further, in a case when a matter to be inspected is a rectangular shape, the maximum diameter when rotating the same corresponds to the diagonal line thereof, therefore, if the longer side of the rectangular is determined as the subscanning direction, the increase of the covering area due to the rotation can be limited.

The moving distance of the inspection table carrying a wafer corresponds to two times of the diameter D of the wafer, in that 2D, in the main scanning direction and no movement in the subscanning direction is required. Further, the covering area by the inspection table in the main scanning direction corresponds to 2D and the covering area in the subscanning direction corresponds substantially to the diameter of D, the amount of the scanning movement in the subscanning direction becomes substantially D/2 and no substantial increase of the covering area is caused. Still further, since the extraneous substance inspection optical system (its extraneous substance inspection area) is disposed at a position on the matter to be inspected corresponding to the head portion thereof in the main scanning direction at the moment when the matter to be inspected is started to move, there occurs for the extraneous substance inspection optical system no increase or bulging-out exceeding the wafer covering area in the main scanning direction.

According to the present invention, the amount of the scanning movement in the subscanning direction is substantially halved as explained above, the throughput for performing the entire surface scanning is improved. Moreover, in the present invention the width of one line for the main scanning is set large in the subscanning direction, a total scanning number is reduced. As a result, time required to perform the entire surface scanning of a matter to be inspected, for example, a wafer is shortened as well as the inspection efficiency for the wafer inspection is enhanced. Further, the covering area represented by the movement area of the inspection table is reduced, in particular, in the wafer extraneous substance inspection the covering area is halved in comparison with the conventional one.

In the present embodiments which will be explained hereinbelow, the extraneous substance inspection optical system is one including a CCD sensor and the main scanning direction is determined as Y direction. Therefore, in the embodiments the major portion of the inspection table is realized as a Y table and an extraneous substance inspection area of the extraneous substance inspection optical system is positioned so as to correspond to the head portion of the wafer at the moment when the wafer is started to move in Y direction. Further, since the wafer is configurated in a circular shape, the extraneous substance inspection area is placed outside the outer configuration of the wafer by positioning a predetermined distance in X direction. As a result, the extraneous substance inspection area is not coincide with the head portion of the wafer. Still further, the rotation of the wafer by 180° after completing the forward main scanning is performed by a Zθ table disposed on the Y table. In the embodiments the control for moving and rotating the table is performed via a table driving circuit by executing a wafer scanning program with a microprocessor (MPU).

BRIEF DESCRIPTION OF THE DRAWINGS

FIGS. 3(a) through 3(c) are schematic views for explaining a manner of scanning in the embodiment wherein FIG. 3(a) is a schematic view for explaining a forward scanning, FIG. 3(b) is a schematic view for explaining a backward scanning and FIG. 3(c) is a schematic view for explaining further subsequent forward scanning;

FIGS. 4(a) and 4(b) are schematic views for explaining a scanning manner in another embodiment in which three detection optical systems are provided in parallel wherein FIG. 4(a) is a schematic view for explaining a forward scanning and FIG. 4(b) is a schematic view for explaining a backward scanning.

DESCRIPTION OF THE PREFERRED EMBODIMENTS

Figure 1:
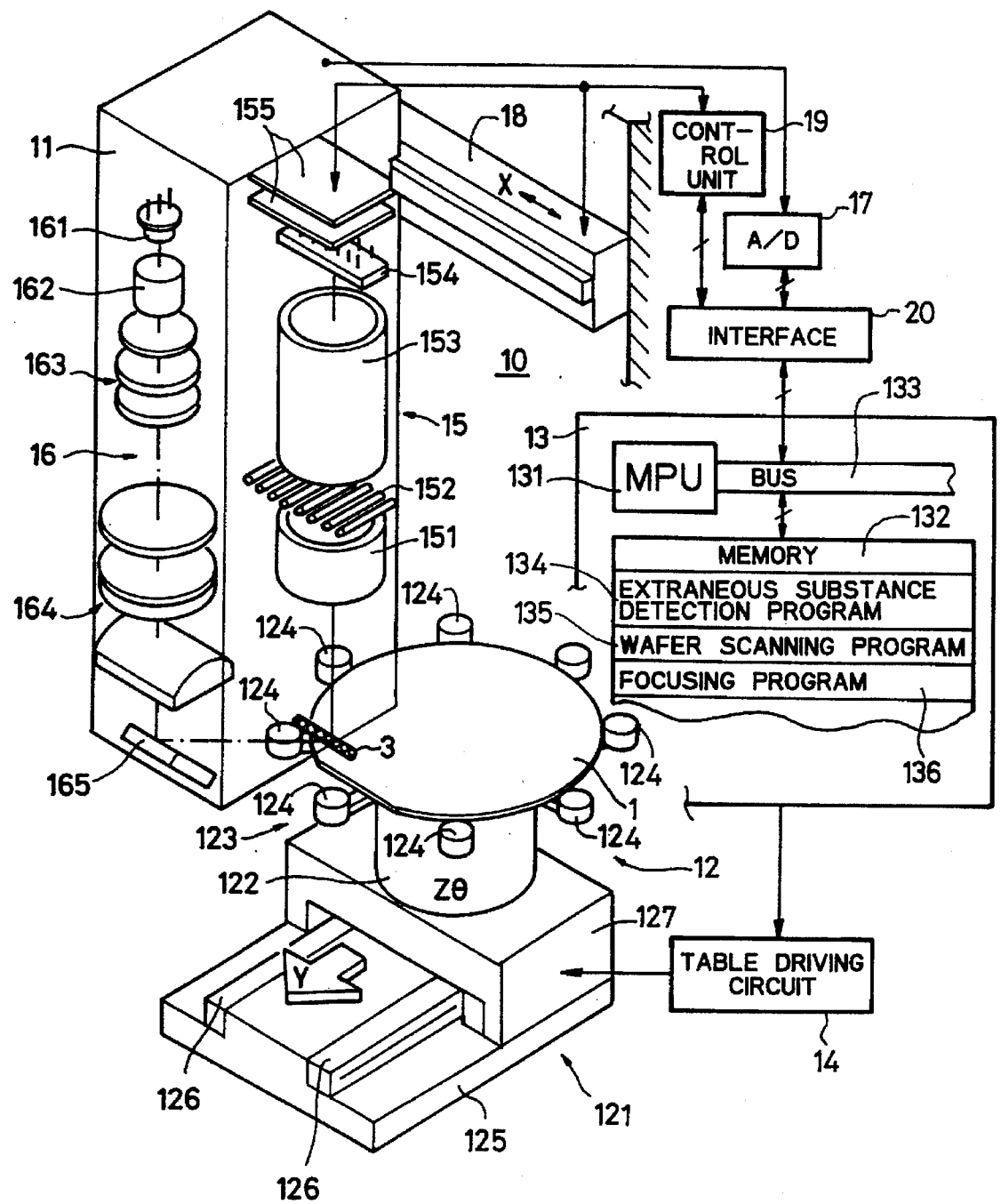
FIG. 1 is a constitutional diagram of one embodiment including a detection optical system as its major part in extraneous substance inspection apparatus according to the present invention.

Numeral 10 in FIG. 1 is an extraneous substance inspection apparatus which is constituted by an extraneous substance inspection optical system 11, an inspection table 12 disposed below the extraneous substance inspection optical system 11, a data processing and control unit 13, a table driving circuit 14, an A/D converter circuit (A/D) 17, an X direction moving mechanism 18, a control unit 19 and an interface 20, and a wafer 1 is carried on the inspection table 12. The control unit 19 generates several control signals for driving such as the X direction moving mechanism 18 and a CCD control and signal reading circuit 155 in response to signals from the data processing and control unit 13 via the interface 20.

The extraneous substance inspection optical system 11, as seen from the illustrated interior thereof, is constituted by a detection optical system 15 and a light projecting optical system 16, and the light projecting optical system 16 irradiates laser beam at an inspection area 3 (extraneous substance detection area) on the wafer 1 having a predetermined width in the subscanning direction. The scattering light above the inspection area 3 is received and detected by the detection optical system 15 which is provided above the inspection table 12 in vertical direction. The extraneous substance inspection optical system 11 is secured to the X direction moving mechanism 18 and is permitted to shift in X direction. The length of the inspection area 3 in X direction corresponds to the width of one line in the main scanning direction. Therefore, the movement pitch in the subscanning direction (X direction) corresponds to the above indicated width.

The light projecting optical system 16 is constituted by a semiconductor laser source 161, condenser lens systems 162, 163 and 164 and a reflection mirror 165 and the laser beam is condensed in an elliptical form corresponding to the inspection are 3 and is irradiated onto the inspection area 3 on the wafer 1 with an elevation angle of about 30° seen from the wafer 1.

The detection optical system 15 is constituted by an objective lens 151 facing the inspection are 3 on the wafer 1, a space filter 152 disposed behind the objective lens 151, a condenser lens system 153 disposed behind the space filter 152, a CCD sensor 154 which is designed to receive an entire picture image of the inspection area 3 image-formed by the condenser lens system 153 and the CCD control and signal reading circuit 155 which reads the detection signals from the CCD sensor 154.

The CCD control and signal reading circuit 155 is controlled by the data processing and control unit 13 via the interface 20 and the control unit 19, reads serially the detection signals detected in response to the intensity of receiving light and transmits the same to the A/D 17, wherein the detected signal is converted into a digital value which is then transmitted to the data processing and control unit 13 via the interface 20 as a detection signal (in digital value).

The detection optical system 15 is positioned in such a manner that an inspection area 3 is located at a position in Y direction corresponding to the head portion of the wafer 1 at the moment when the wafer 1 is started to move in the main scanning direction (Y direction). Since the wafer 1 is configurated in a circular shape, a part of the inspection area 3 can be placed outside the outer configuration of the wafer 1, the inspection area 3 is illustrated somewhat inner side in X direction and somewhat inner side of the actual head portion of the wafer 1 for the sake of illustration and explanation convenience.

The data processing and control unit 13 is normally constituted by such as a MPU 131 and a memory 132, receives the signals from the A/D 17 via the interface 20 and a bus 133 and stores the same in the memory 132. The memory 132 stores several types of programs including an extraneous substance detection program 134, a wafer scanning program 135 and a focusing program 136.

The table driving circuit 14 is a driving circuit which reciprocally moves the inspection table 12 in Y direction in response to the execution of the wafer scanning program 135 by the MPU 131. Further, at the moment when completing the movement corresponding to the diameter D of the wafer 1+α(α represents a margin for the scanning) in Y direction, a Zθ table 122 is turned by 180° and the table driving circuit 14 causes the inspection table 12 a backward movement corresponding to the diameter D+α in Y direction. Namely, the table driving circuit 14 is a driving circuit which causes a reciprocative scanning over the wafer 1 in Y direction and rotation thereof.

The inspection table 12 is constituted by a Y table 121, the Zθ table 122 and a center positioning mechanism 123 provided at the Zθ table 122. The center positioning mechanism 123 is a restriction mechanism including a plurality of rollers 124 arranged along the outer circumference of the wafer 1. Since the plurality of rollers 124 are designed to permit an interlocked rotation from the outside to the inside like so called shutter diaphrams, the center of the wafer 1 carried on the inspection table 12 is positioned at the center of the inspection table 12.

The Y table 121 is constituted by a base plate 125, rails 126 provided on the base plate 125 and a table 127 which is designed slidable on the rails 126 in Y direction.

The Zθ table 122 is a table carried on the table 127 and movement of the Zθ table 122 in Z direction is performed by an elevation mechanism provided inside the table 127 and secured thereto. The elevation mechanism primarily moves the wafer 1 in vertical direction for focusing and sets the vertical position of the wafer 1.

Figure 2:
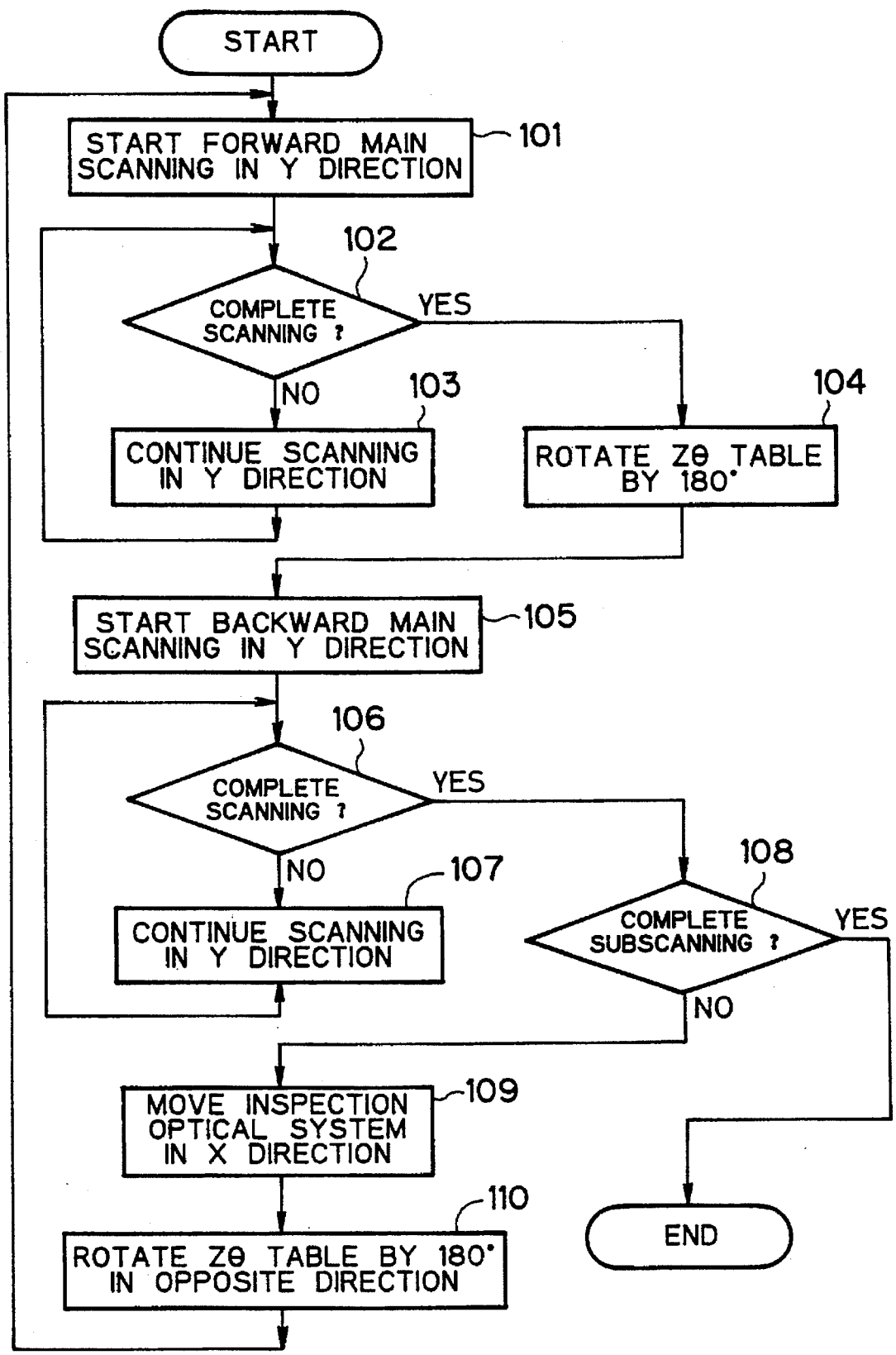
FIG. 2 is a flow chart of the scanning processing performed in the embodiment.

FIG. 2 is a flow chart for scanning processing executed by the wafer scanning program 135, wherein through driving the Y table the forward scanning in Y direction is started (step 101), a judgement whether or not a scanning in Y direction corresponding to the diameter D+α has been completed is performed (step 102), if such scanning has not yet completed, the answer is NO and the Y table is further moved in Y direction (step 103), and the above judgement is again performed at step 102. If it is judged in this circulating loop that one forward main scanning in Y direction has been completed, the answer changes to YES and the Zθ table is rotated by 180° (step 104), the Y table is driven in the direction opposite to the previous direction to start the backward scanning in Y direction (step 105), then a judgement whether or not the backward scanning corresponding to the diameter D+α in Y direction has been completed is performed (step 106), and if not completed, the answer is NO and the Y table is further moved in Y direction (107), then the judgement in step 106 is again performed. When it is judged in this circulating loop that one backward scanning has been completed, the answer changes to YES, then a judgement whether or not a subscanning has been completed is performed by the MPU 131 depending on the determined position in X direction of the extraneous substance inspection optical system 11 (step 108).

In this step, if a predetermined movement in the subscanning direction has not been completed, the X direction movement mechanism 18 is driven to move toward the inside of the wafer 1 by a predetermined subscanning amount corresponding to the inspection area 3 and to move the extraneous substance inspection optical system 11 by one pitch (an amount substantially corresponding to the width of the inspection area 3) in the subscanning direction (step 109). Thereafter, the Zθ table is rotated in opposite direction by 180° to return the same to its original condition (step 110). Thus, the process returns to step 101, and the above explained processes are restarted and are repeatedly executed until the predetermined subscanning has been completed.

If it is judged at step 108 that the predetermined subscanning has been completed, the processing ends. The completion of the subscanning is judged when the extraneous substance inspection optical system 11 moves toward the inside of the wafer 1 and either forward or backward scanning over the area including a center line passing the center of the wafer 1 has been performed which represents the last scanning for the entire surface scanning of the wafer 1 and the extraneous substance inspection optical system 11 has been positioned at a predetermined position in X direction.

Further, the 180° rotation of the Zθ table at step 110 can be performed in the same direction as at step 104 for every forward and backward main scanning. During the forward and backward main scanning the MPU 131 executes the extraneous substance detection program 134, in that based on the detection signals (digital values) received from the A/D 17, the MPU 131 judges at which position in the inspection area 3 with respect to the light receiving position (the position of light receiving pixel) of the CCD sensor 154 an extraneous substance exists or no extraneous substances exist in the inspection area 3 and performs extraneous substance detection. In an actual application, it is preferable to use a one line sensor having about 5,000 pixels in subscanning direction as the CCD sensor 154.

Figure 3A:
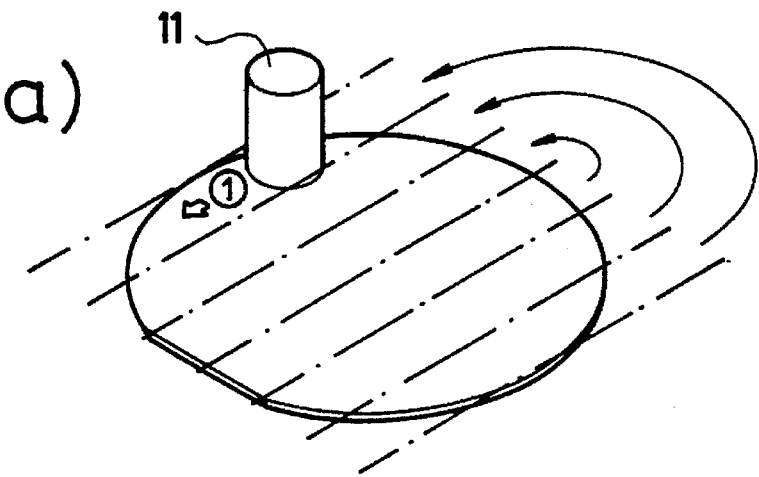
Figure 3B:
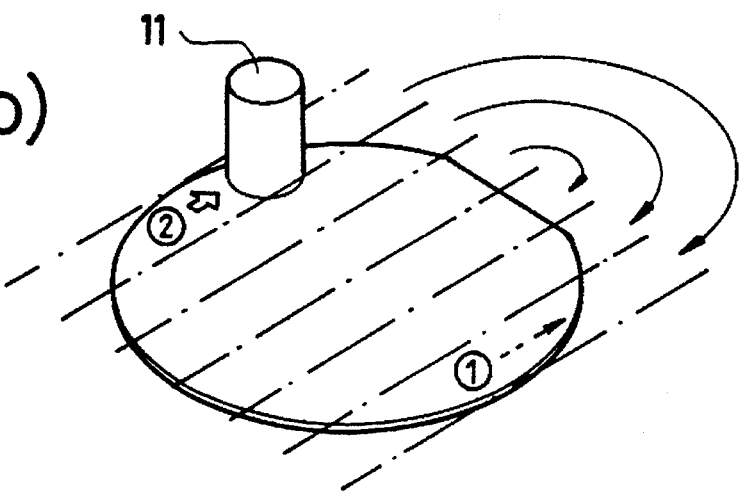
Figure 3C:
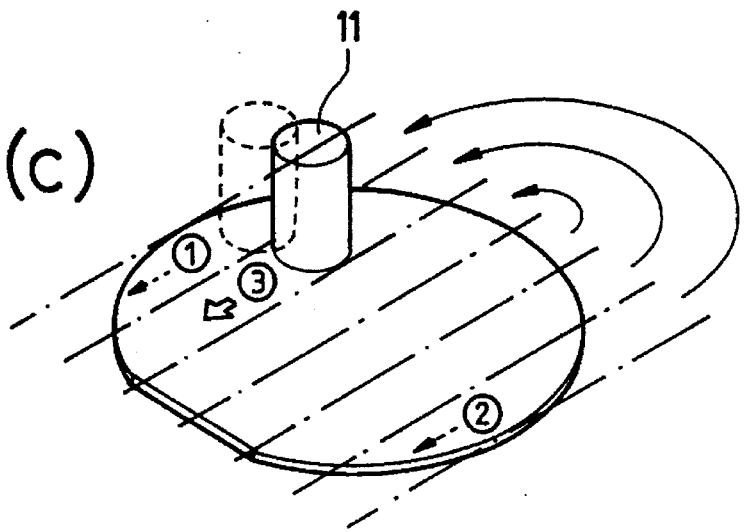

FIGS. 3(a) through 3(c) show the order of the forward and backward scanning in the above explained processing with numerals (1), (2) and (3). FIG. 3(a) shows the first forward scanning state, FIG. 3(b) shows the first backward scanning state and FIG. 3(c) shows the subsequent forward scanning state. As seen from FIG. 3(c), the scanning area on the wafer 1 results in the order of (1), (2) and (3). Arrows in FIGS. 3(a) through 3(c) represent direction of 180° rotation of the wafer 1 after completing respective main scannings. Therefore, in the present embodiment at the completion of the first main scanning the wafer 1 is rotated in anti-clockwise direction by 180° and at the completion of the backward main scanning the wafer 1 is rotated in clockwise direction by 180° to return to the original condition. The 180° rotation is repeated alternatively in normal and reverse directions for every forward and backward main scanning.

In the embodiment, for the main scanning, the table moves reciprocally in the main scanning direction, the table is alternatively rotated by 180° in normal and reverse directions at the time between the forward and backward scannings, however the table maybe rotated by 180° in the same direction at the time between the forward and backward scannings. As a result, the scanning direction for the wafer 1 is equated for both the forward scanning and the backward scanning. In the drawings dotted arrows indicate the directions of already completed scannings.

Figure 4A:
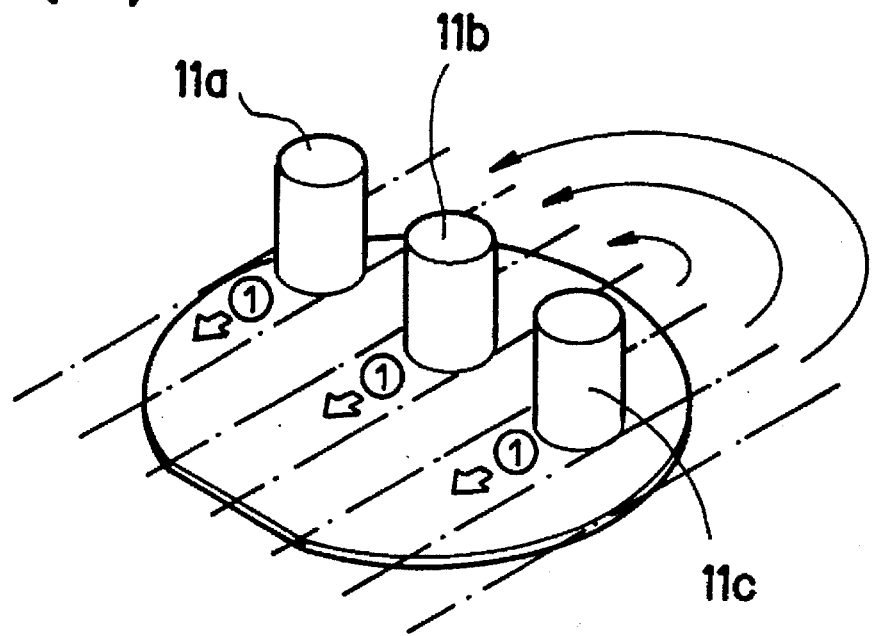
Figure 4B:
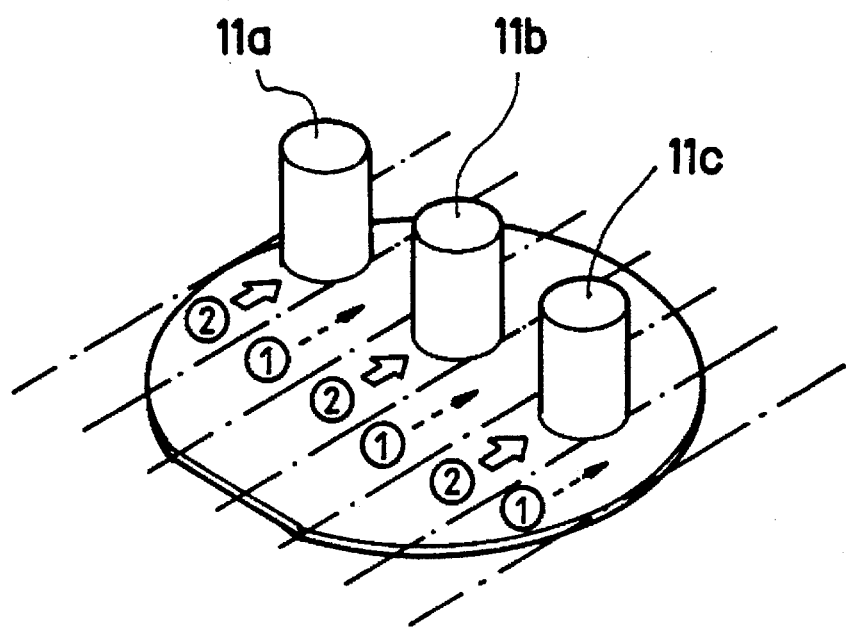
Figure 5:
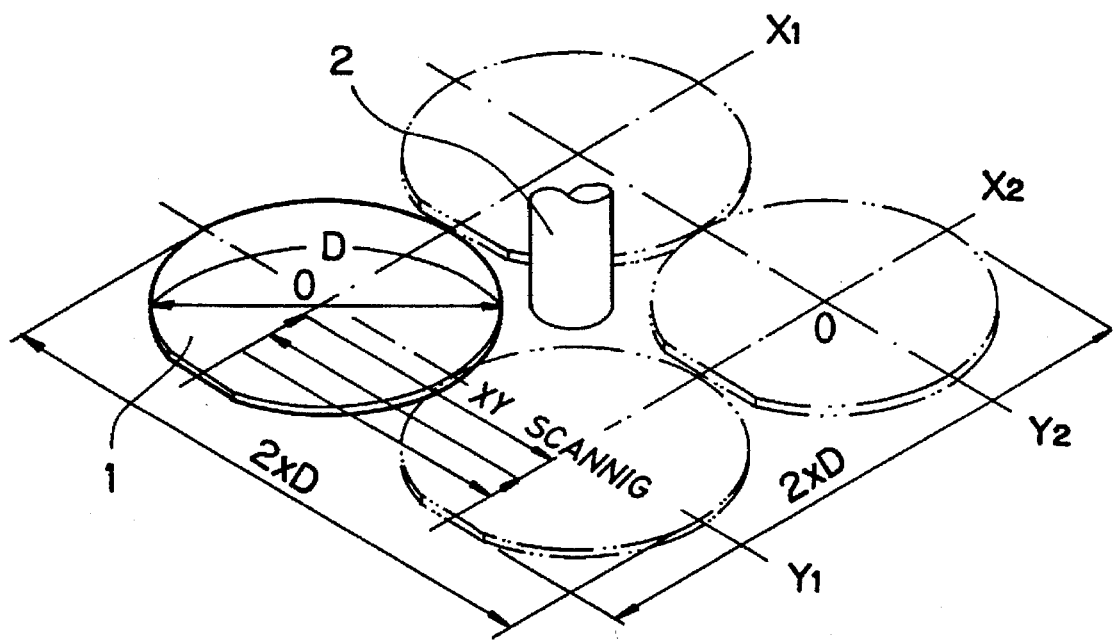
FIG. 5 is a schematic view for explaining the movement range of an inspection table in a conventional XY scanning type extraneous substance inspection apparatus.

FIGS. 4(a) and 4(b) shows another embodiment in which a plurality of extraneous substance inspection optical systems 11 are arranged in the subscanning direction, thereby the movement of the extraneous substance inspection optical system 11 in the subscanning direction is eliminated.

In the present embodiment, the width in the subscanning direction substantially corresponds to a width determined by dividing equally the diameter D of the wafer 1 with 2N (in the present embodiment, N=3 therefore, divided equally into 6). N(=3) units of extraneous substance detection optical systems 11 are arranged with a gap corresponding to the width (subscanning width) determined by the 2N division. Herein the subscanning width substantially corresponds to the length of the inspection area 3.

The three extraneous substance detection optical systems in the present embodiment are represented by numerals 11a, 11b and 11c, and each corresponds to the extraneous substance detection optical system 11 as shown in FIG. 1. Therefore, at the time when the main scanning in Y direction has been completed as shown in FIG. 4(a), the wafer 1 is rotated by 180° in the direction shown by arrows (in anti-clockwise direction and thereafter a backward main scanning is performed as shown in FIG. 4(b) through which the scanning over the entire surface of the wafer 1 is completed.

In the present embodiment, respective detection signals from the extraneous substance detection optical systems 11a, 11b and 11c are converted into digital values by three A/Ds (not shown, but each A/D corresponds to A/D 17 in FIG. 1) provided for the respective extraneous substance detection optical systems and are input in parallel into the data processing and control unit 13 via the interface 20.

Now, in the present embodiment the subscanning width substantially corresponds to the width determined by dividing equally the diameter of the wafer with 2N, however, with regard to the first scanning and the subsequent scanning or the final scanning the scanning area is not necessarily required to meet the outer configuration of the wafer. Therefore the length which is to be divided by 2N can be larger than the diameter D of the wafer. However, the length is at most the diameter of wafer+one subscanning width. Accordingly, a length between the diameter D of the wafer and the diameter D of the wafer+one subscanning width can be divided equally by 2N.

In the above embodiments, wafers are primarily represented as the matters to be inspected, however the present invention can be applied to matters having non-circular shape unlike the wafers as explained.

We claim:

1. An extraneous substance inspection method comprising the steps of:

positioning an extraneous substance inspection optical system having an extraneous inspection area of a predetermined scanning width in subscanning direction of a matter to be inspected in such a manner that the extraneous substance inspection area at a moment when the matter to be inspected is started to move in main scanning direction is arranged at a position in the main scanning direction corresponding to a head portion of the matter to be inspected;

moving the matter to be inspected in the main scanning direction to perform a forward scanning for the matter to be inspected to thereby detect possible extraneous substances in the extraneous substance inspection area; and, rotating the matter to be inspected by 180° after completing the forward scanning, then moving the matter to be inspected in the direction opposite to the forward scanning to perform a backward scanning, to thereby detect possible extraneous substances in the extraneous substance inspection area.

2. An extraneous substance inspection method according to claim 1 further comprising the steps of:

moving the extraneous substance inspection optical system by substantially the predetermined scanning width in the subscanning direction after completing the backward scanning; and, then rotating the matter to be inspected by 180° to perform a subsequent forward scanning.

3. An extraneous substance inspection method according to claim 2, wherein the matter to be inspected is a semiconductor wafer, the forward and backward scannings are performed in a plurality of times and the semiconductor wafer is rotated by 180° in the first and second direction alternatively after every completion of the forward and backward scannings.

4. An extraneous substance inspection method according to claim 1, wherein a plurality of the extraneous substance inspection optical systems are provided and the plurality of the extraneous substance inspection optical systems are arranged in the subscanning direction with a gap corresponding to the predetermined scanning width.

5. An extraneous substance inspection method according to claim 4, wherein the matter to be inspected is a semiconductor wafer and the predetermined scanning width corresponds to a width determined by driving equally a length between the diameter of the semiconductor wafer and the diameter of the semiconductor wafer plus the predetermined scanning width with 2N (wherein N is an integer equal to or more than 2), and further N units of the extraneous substance inspection optical systems are provided and are arranged with a gap corresponding to the predetermined scanning width.

6. An extraneous substance inspection apparatus which scans in two dimensions over a matter to be inspected and detects possible extraneous substances thereon comprising:

an extraneous substance inspection optical system having an extraneous inspection area of a predetermined scanning width in subscanning direction of the matter to be inspected and positioned in such a manner that the extraneous substance inspection area at a moment when the matter to be inspected is started to move in main scanning direction is arranged at a position in the main scanning direction corresponding to a head portion of the matter to be inspected;

a moving and rotating mechanism which carries the matter to be inspected thereon, moves reciprocatively the matter to be inspected in main scanning direction and rotates the matter to be inspected by substantially 180° around the substantial center thereof; and, a control unit which controls said moving and rotating mechanism in such a manner that the matter to be inspected is subjected to a forward scanning in the main scanning direction, rotated by 180° after completing the forward scanning in the main scanning direction and further subjected to a backward scanning in the main scanning direction, whereby possible extraneous substances in the respective extraneous substance inspection areas are detected via the forward scanning and the backward scanning.

7. An extraneous substance inspection apparatus according to claim 6 further comprising:

a subscan moving mechanism which substantially moves said extraneous substance inspection optical system by the predetermined scanning width in the subscanning direction, said moving and rotating mechanism rotates the matter to be inspection by 180° in addition to the rotation of 180° and said control unit controls said subscan moving mechanism so as to move said extraneous substance inspection optical system by substantially the predetermined scanning width in the subscanning direction after completing the backward scanning and controls said moving and rotating mechanism so as to rotate the matter to be inspected by 180° in a second direction opposite to the first direction.

8. An extraneous substance inspection apparatus according to claim 7, wherein the matter to be inspected is a semiconductor wafer, and said control unit causes to perform the forward and backward scannings in a plurality of times and controls the semiconductor wafer to rotate by 180° in the first and second direction alternatively after every completion of the forward and backward scannings.

9. An extraneous substance inspection apparatus according to claim 6, wherein a plurality of said extraneous substance inspection optical systems are provided and are arranged in the subscanning direction with a gap corresponding to the predetermined scanning width.

10. An extraneous substance inspection apparatus according to claim 9, wherein the matter to be inspected is a semiconductor wafer and the predetermined scanning width corresponds to a width determined by driving equally a length between the diameter of the semiconductor wafer and the diameter of the semiconductor wafer plus the predetermined scanning width with 2N (wherein N is an integer equal to or more than 2), and further N units of said extraneous substance inspection optical systems are provided and are arranged with a gap corresponding to the predetermined scanning width.

* * * * *